US00RE39746E

(19) United States
(12) Reissued Patent
Boinowitz et al.

(10) Patent Number: US RE39,746 E
(45) Date of Reissued Patent: *Jul. 31, 2007

(54) PHOSPHORIC ESTERS AND THEIR USE AS DISPERSANTS

(75) Inventors: Tammo Boinowitz, Essen (DE); Eberhard Esselborn, Essen (DE); Arno Knebelkamp, Mühlheim (DE); Christian Psiorz, Düsseldorf (DE); Stefan Silber, Krefeld (DE); Stefan Stadtmüller, Essen (DE); Ellen Wallhorn, Bochum (DE)

(73) Assignee: Goldschmidt GmbH, Essen (DE)

( * ) Notice: This patent is subject to a terminal disclaimer.

(21) Appl. No.: 10/853,763

(22) Filed: May 25, 2004

Related U.S. Patent Documents

Reissue of:
(64) Patent No.: 6,423,130
Issued: Jul. 23, 2002
Appl. No.: 09/829,799
Filed: Apr. 10, 2001

U.S. Applications:
(62) Division of application No. 09/251,966, filed on Feb. 17, 1999, now Pat. No. 6,310,123.

(30) Foreign Application Priority Data

Feb. 19, 1998 (DE) ..... 198 06 964

(51) Int. Cl.

| | |
|---|---|
| ***C08K 5/372*** | (2006.01) |
| ***C08K 5/52*** | (2006.01) |
| ***B01F 17/14*** | (2006.01) |
| ***B01F 3/12*** | (2006.01) |
| ***C07F 9/09*** | (2006.01) |

(52) U.S. Cl. ..... 106/476; 106/503; 516/33; 516/34; 516/77; 516/81; 516/90; 516/93; 516/199; 516/908; 524/141; 524/513; 524/522; 524/115; 524/136; 525/333.3; 525/340; 558/186; 526/932

(58) Field of Classification Search ..... 558/186, 558/92, 110, 114; 516/13, 24, 34, 57, 199, 516/908, 33, 77, 78, 90, 93, 81; 106/476, 106/503; 524/115, 136, 141, 494, 513, 522; 525/340, 333.3; 528/393; 526/932
See application file for complete search history.

(56) References Cited

U.S. PATENT DOCUMENTS

| | | | | | |
|---|---|---|---|---|---|
| 3,076,011 | A | * | 1/1963 | Hamermesh et al. | 558/194 |
| 3,112,335 | A | * | 11/1963 | Ronay et al. | 558/105 |
| 3,978,160 | A | * | 8/1976 | Seiler et al. | 525/385 |
| 4,720,514 | A | * | 1/1988 | Needham | 523/351 |
| 4,986,851 | A | * | 1/1991 | Dietz et al. | 106/503 |
| 5,002,686 | A | * | 3/1991 | Guth et al. | 510/339 |
| 5,104,983 | A | * | 4/1992 | Stock et al. | 524/141 |
| 5,126,474 | A | * | 6/1992 | Topfl | 558/34 |
| 5,130,463 | A | * | 7/1992 | Haubennestel et al. | 558/172 |
| 5,151,218 | A | * | 9/1992 | Haubennestel et al. | 516/77 |
| 5,484,851 | A | * | 1/1996 | Fock | 525/333.5 |
| 5,914,072 | A | * | 6/1999 | Zirnstein et al. | 516/57 |
| 6,159,390 | A | * | 12/2000 | Fichou et al. | 252/182.24 |
| 6,310,123 | B1 | * | 10/2001 | Boinowitz et al. | 524/141 |
| 6,689,731 | B2 | * | 2/2004 | Esselborn et al. | 510/288 |

FOREIGN PATENT DOCUMENTS

| | | | |
|---|---|---|---|
| JP | 58-100194 | * | 6/1984 |
| JP | 59-100194 | * | 6/1984 |

OTHER PUBLICATIONS

Eastman Laboratory Chemicals (Eastment Chemical Co., Laboratory and research Products, Rochester, NY) pp. 919 and 977, Apr. 1994.*

DWPI on West, week 198429, London: Derwent Publications Ltd., AN 1984–179609 JP 59100194 A (Kao Corp.), Abstract, 1984.*

Martin Mosquet et al., "Polyoxyethylene Di–Posphonates as Efficient Dispersing Polymers to Aqueous Suspensions", Journal of Polymer Science, vol. 65, pp. 2545–2555 (1977), month unavailable.*

TBK Trading, LLC on the World Wide Web at http://www.tbktrading.com/FAQ.htm#Dye%20and%20a%20Pigment (Apr. 2005) pp. 1–3.*

* cited by examiner

*Primary Examiner*—Daniel S. Metzmaier
(74) *Attorney, Agent, or Firm*—Scully, Scott, Murphy & Presser, P.C.

(57) ABSTRACT

The invention relates to phosphoric esters of the general formula I (I)

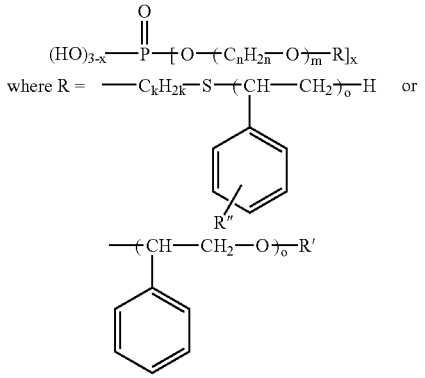

where X is 1 or 2; n is from 2 to 18; m and o are each from 2 to 100; k is from 2 to 4; R" is H or a linear or branched alkyl radical; and R' is an alkyl, alkaryl, alkenyl, or sulfopropyl radical, and to there use as dispersants for pigments and fillers in aqueous or organic media.

19 Claims, No Drawings

PHOSPHORIC ESTERS AND THEIR USE AS DISPERSANTS

Matter enclosed in heavy brackets [ ] appears in the original patent but forms no part of this reissue specification; matter printed in italics indicates the additions made by reissue.

RELATED APPLICATIONS

The present application is a divisional application of U.S. application Ser. No. 09/251,966, filed Feb. 17, 1999, now U.S. Pat. No. 6,310,123.

FIELD OF THE INVENTION

The present invention relates to phosphoric esters a) obtainable by reacting an ω-hydroxy-functional oligo- or poly(alkyl)styrene with an alkylene oxide to give a poly(alkyl)styrene-block(b)-polyalkylene oxide copolymer and then converting said copolymer into the corresponding phosphoric esters with a phosphorus compound which forms phosphoric esters, up to 100% of the terminal hydroxyl groups of said poly(alkyl) styrene-block(b)-polyalkylene oxide copolymer being reacted to give phosphoric ester groups and the phosphorus atoms, depending on the chosen stoichiometric proportions, being mono- and/or diesterified, or b) based on polystyrene oxide-block(b)-polyalkylene oxide copolymers obtainable starting from a monofunctional starter alcohol by sequential addition of styrene oxide and of an alkylene oxide in accordance with the desired sequence and chain length of the individual segments and subsequently by reaction to give the corresponding phosphoric esters, in the manner described in a).

The invention relates, furthermore, to the preparation of these phosphoric esters and to their use as dispersants for pigments and fillers.

BACKGROUND OF THE INVENTION

For the dispersion of fillers and pigments in liquid media it is common to operate with the aid of dispersants in order to reduce the mechanical shear forces required for effective dispersion of the solids and at the same time to obtain very high degrees of filling.

The dispersants support the disruption of agglomerates, wet and/or cover, as surface-active materials, the surface of the particles to be dispersed, and stabilize the particles against unwanted reagglomeration.

Dispersants have become indispensable for the preparation, for example, of highly concentrated color pastes for the paints and coatings industry, for the preparation of pigment concentrates (masterbatches) for the coloring of articles made of plastic, and for the processing of unsaturated polyester resins (UP resins) which comprise large amounts of calcium carbonate or aluminum hydroxide (ATH) as fillers.

The combination of very high degrees of filling in association with a very low viscosity is of particular interest for the producers and users of these products on primarily economic grounds. In the case of the fillers, these commonly constitute the least expensive formulating component; pigment concentrates are intended by the plastics processor to be used for coloring in very highly concentrated form—that is, as far as possible without additional carrier materials.

Phosphoric esters and their use as dispersants are known and can be found in the prior art. For instance, U.S. Pat. No. 4,720,514 describes phosphoric esters of a range of alkylphenol ethoxylates, which can be used with advantage to formulate aqueous pigment dispersions. Phosphoric esters for similar use are described in EP-A-0,256,427, U.S. Pat. No. 5,130,463 and U.S. Pat. No. 5,151,218 report phosphoric esters based on hydroxy-terminated polyaddition products and polycondensation products, which are used for the preparation of highly filled polyester molding compounds, especially for SMC and BMC formulations (SMC=sheet molding compounds; BMC=bulk molding compounds). Bifunctional phosphoric esters prepared by the Mannich-Moedritzer reaction, and their adsorption characteristics on calcium carbonate, are described in J. Appl. Polym. Sci. 65, 2545 (1997).

The known phosphoric esters, however, have the disadvantage that in general they are not universally applicable since there is in many cases a lack of adequate compatibility between the dispersing additive and binder or between the dispersing additive and the surrounding medium (aqueous or solvent-containing formulations). The chemical composition of the phosphoric esters also has a large part to play: in aqueous formulations it is preferred to use only those phosphoric esters whose molecule carries no additional hydrolyzable functional groups, such as ester or urethane groups. Frequently, high levels of dispersing additives are required in order to suppress the incidence of agglomerates; the degrees of filling which can be achieved are unsatisfactorily low, the stability of the dispersions and thus the permanence of the viscosity is often inadequate, and flocculation and aggregation cannot always be avoided, possibly resulting in visible separation and in flow defects and surface defects.

BRIEF SUMMARY OF THE INVENTION

It is therefore an object of the present invention to overcome a large number of the above disadvantages and in so doing to achieve not only the viscosity reduction of highly filled dispersions that is important for processability but also improved compatibility with the surrounding medium.

This object is surprisingly achieved through the use of phosphoric esters of amphiphilic block copolymers having the characteristic structural feature of a poly(alkyl)styrene segment and/or a polystyrene oxide segment to which a polyalkylene oxide segment is attached.

The invention accordingly provides phosphoric esters of the general formula I (I)

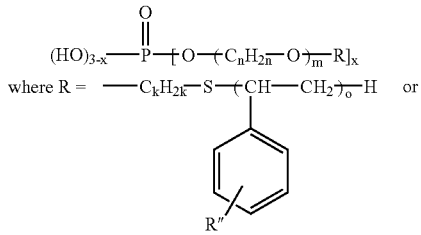

-continued

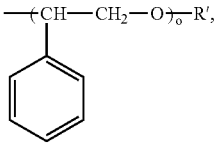

x is 1 or 2, n is a number from 2 to 18, m and o are each a number from 2 to 100, k is a number from 2 to 4, R" is H or a linear or branched alkyl radical which may if desired be substituted by additional functional groups, and R' is an alkyl, alkaryl, alkenyl or sulfopropyl radical.

DETAILED DESCRIPTION OF THE INVENTION

Preferably R"=H.

R' is commonly derived from an alcohol R'OH which functions as the starter alcohol for the polymerization of the styrene oxide and alkylene oxide.

Examples of the radicals R' are the methyl, butyl, stearyl, allyl, hexenyl, nonylphenyl and oleyl radicals.

Methyl and butyl radicals are preferred for R'.

Where n=2 the polyether radical contains exclusively ethylene oxide units. Where n>2, the polyether radical consists of ethylene oxide units and, proportionally, of oxyalkylene units whose carbon number is between 3 and 18. In this case n can adopt the value of a fractional number between 2 and 18. Preferably, the oxyalkylene block consists of ethylene oxide units, with the additional presence if desired of oxybutylene units in addition to the oxypropylene units. Oxyalkylene units having a carbon number of from 4 to 18 are preferred when, in addition, it is desired for the product to have oleophilic properties.

The average molecular weight of the phosphoric esters of the invention lies within the range from 300 to about 15,000 g/mol, preferably from 500 to 5000 g/mol. It can be determined with great ease by the customary methods of polymer analysis, both for the phosphoric esters and for the amphiphilic block copolymers. The ratio of m to o is from 1:50 to 50:1, preferably from 1:10 to 10:1 and, with particular preference, from 1:2 to 10:1.

Examples of suitable phosphoric esters are:

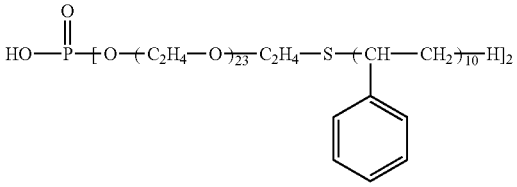

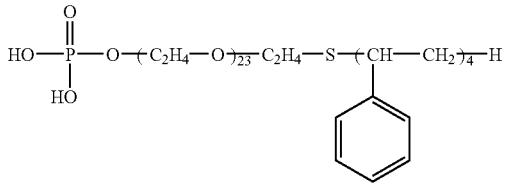

-continued

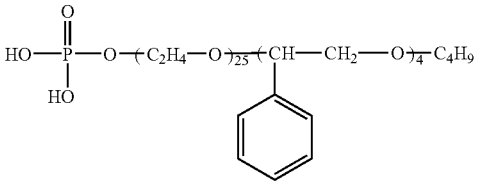

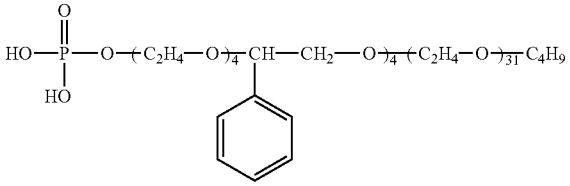

Starting materials used to prepared the phosphoric esters of the invention are, accordingly, amphiphilic block copolymers of the general structures:

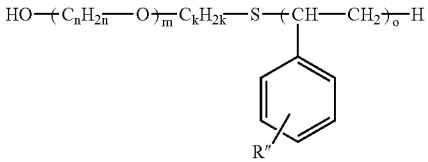

and

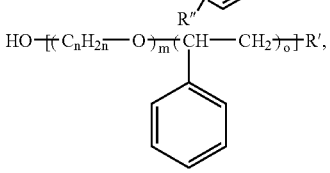

respectively, where the radicals R" and R' and the indices m, k, n and o are as defined above.

These block copolymers are prepared by reacting the terminal hydroxyl group with a phosphorus compound which forms phosphoric esters, to give the phosphoric esters of the invention.

Block copolymers of this kind are described, for example, in DE-A-41 34 967. The polystyrene-b-polyalkylene oxide copolymers of type A-B are prepared by first subjecting styrene to free-radical polymerization in the presence of sufficient amounts of an initiator and of an amount, corresponding to the desired chain length, of a chain regulator which carries not only a mercapto group but also another functional group having an active hydrogen radical, generally a hydroxyl group, and subjecting the resulting polymer to an addition reaction at temperatures from 20 to 180° C. with alkylene oxide until the desired molecular weight in the block B is reached.

The corresponding polystyrene oxide-b-polyalkylene oxide copolymers are prepared, starting from the starter alcohol R'OH, by subjecting the corresponding alkylene oxides to a sequential addition reaction in accordance with the desired sequence and chain length of the individual segments so as to give a blocklike structure.

Both synthetic routes lead to a amphiphilic block copolymers having a terminal hydroxyl group, both including, as an additional, characteristic structural element, a hydrophobic segment composed of aromatic groups. The processes described make it possible in a simple manner to adapt the chain lengths m and o of the individual segments, the overall molecular weight and the ratio m/o of aromatic to nonaromatic segments to the technical requirements of the particular application. For instance, products employed for applications in aqueous systems are preferably those whose polyalkylene oxide segment is composed of ethylene oxide units. Conversely, products having a relatively high proportion of styrene units and/or styrene oxide units have proven particularly suitable for dispersion processes in a very hydrophobic environment, such as, for example, paraffin oils, or in a polyolefin melt.

The reaction to give the phosphoric esters of the invention takes place by reaction of the terminal hydroxyl groups with a phosphorus compound which forms phosphoric esters, in a manner known per se. Examples of suitable phosphorus compounds are phosphorus pentoxide, phosphoryl chloride or polyphosphoric acids of the general formula $H_{n+2}P_nO_{3n+1}$. For the preparation of the phosphoric esters it is particularly preferred to employ a commercially available polyphosphoric acid (Merck) having a content of about 85% $P_4O_{10}$. The reaction generally takes place without solvent at temperatures from about 80 to 100° C. To remove any traces of moisture present it is possible first of all to remove residues of water from the system using an inert solvent, such as toluene or xylene, for example, prior to the reaction with the polyphosphoric acid. Alternatively, in principle, the reaction can be carried out in the presence of solvents or solvent mixtures. This is always advantageous when the phosphoric esters of the invention have to be formulated in inert solvents or solvent mixtures in accordance with their subsequent use.

The extent of esterification of the terminal hydroxyl group of the amphiphilic block copolymers which is the target of esterification in the esterification reaction is preferably from 50 to 100%; with particular preference, esterification is quantitative. Depending on the amount of phosphorus compound which forms phosphoric esters, employed relative to the hydroxyl equivalent of the block copolymers, the products of the esterification are alternatively preferably monoesters, diesters, or mixtures of monoesters and diesters.

Depending on the pH of the medium employed, the phosphoric esters of the invention may also be present in partially or fully neutralized form.

The dispersants can either be applied directly to the solids that are to be dispersed or else can be added to the aqueous and/or organic medium. They can be distributed in pure form or as a masterbatch in relatively high concentration in an organic medium. It is of course also possible to employ the dispersants to be used in accordance with the invention together with further auxiliaries or dispersants, such as, for example, with the stearates known as dispersants.

Appropriate solids are mineral fillers, such as talc, calcium carbonate, dolomite, mica, wollastonite, kaolin, and mineral flame retardants, such as aluminum hydroxide or magnesium hydroxide. Suitable pigments are carbon black or titanium dioxide, the latter also being employable in finely divided form as a UV protectant in cosmetic formulations. Further dispersible solids are chemical blowing agents, such as azodicarbonamide, or mixtures of solid acids and carbonates.

The dispersants to be used in accordance with the invention can also be employed for dispersing ceramic materials in organic media, such as, for example, finely divided alumina, silicon carbide or silicon nitride.

Suitable organic media include polyethylene, polypropylene, polystyrene, polyamides, polyesters, poly (meth)acrylates, polyvinyl chloride, unsaturated polyesters, and liquid paraffins.

The dispersants of the invention are particularly suitable for enhancing the distribution of finely divided solids in elastomers, thermoplasts, thermosets and polymer blends.

The phosphoric esters of the invention have proven particularly suitable as dispersants for the preparation of highly filled SMC and BMC molding compounds. SMCs (sheet molting compounds) and BMCs (bulk molding compounds) consist of unsaturated polyester resins, a thermoplastic component, glass fibers, and fillers. The unsaturated polyester resin and the thermoplastic component (polystyrene is frequently used as the thermoplastic component) are usually dissolved in monomeric styrene which, in the course of processing by compression or injection molding, cures and forms a three-dimensional network structure with the unsaturated polyester resin. The addition of glass fibers leads to high tensile strength and rigidity; the fillers guarantee high compressive strength and are responsible, moreover, for good dimensional stability and low thermal expansion.

With the phosphoric esters of the invention a very low viscosity is achieved even at very high degrees of filling. The formulations feature absolute freedom from inhomogeneities and a high level of stability on storage.

In addition, the phosphoric esters of the invention can be used to prepare aqueous pigment pastes. For this purpose, use is made of from 0.1 to 200% by weight of the phosphoric esters, preferably from 0.5 to 100% by weight (based on the weight of the pigments). In the case of use in accordance with the invention the phosphoric esters can either be mixed beforehand with the pigments to be dispersed or else can be dissolved directly in the aqueous or solvent-containing dispersion medium prior to or simultaneously with the addition of pigments and any other solids.

Examples of pigments which can be mentioned in this context are organic and inorganic pigments, including carbon blacks.

As inorganic pigments mention may be made by way of example of titanium dioxides and iron oxides. Examples of organic pigments which may be considered are azo pigments, metal complex pigments, anthraquinonoid pigments, phthalocyanine pigments, polycyclic pigments, especially those of the thioindigo, quinacridone, dioxazine, pyrrolopyrrole, naphthalenetetracarboxylic acid, perylene, iso-amidolin(on)e, flavanthrone, pyranthrone or isoviolanthrone series. With particular preference, the dispersing additives of the invention are suitable for preparing aqueous carbon black (gas black) pastes.

Examples of fillers which can be dispersed in aqueous coating materials are those, for example, based on kaolin, talc, other silicates, chalk, glass fibers, glass beads, or metal powders.

Suitable coating systems in which the pigment pastes of the invention can be incorporated are any desired aqueous 1- or 2-component coating materials. Examples which may be mentioned are aqueous 1-component coating materials, such as those based on alkyd, acrylate, epoxy, polyvinyl acetate, polyester or polyurethane resins, or aqueous 2-component coating materials, examples being those based on hydroxyl-containing polyacrylate or polyester resins with melamine resins or, if desired, blocked polyisocyanate resins as crosslinkers. Similarly, polyepoxy systems may also be mentioned.

In the examples below, the preparation of the compounds to be used in accordance with the invention is described first of all. This is followed by performance examples demonstrating the properties of the compounds to be used in accordance with the invention and, for comparison, properties obtainable with some prior art products.

It is obvious and conventional to the skilled worker that these examples represent merely a selection of the possibilities which exist and are in no way to be regarded as a limitation.

PREPARATION EXAMPLES

1) Preparation of polystyrene-b-polyalkylene oxide copolymers (in analogy to DE-A-41 34 967, not in accordance with the invention) as starting materials for the preparation of the corresponding phosphoric esters of the invention a) Preparation of a polystyrene-b-polyalkylene oxide copolymer (in analogy to DE-A-41 34 967)

100 g of xylene are heated to 120° C. under a nitrogen atmosphere in a reactor which is fitted with a stirrer. Over the course of 3 hours, while maintaining the temperature of 120° C., a mixture of 1350 g (about 13 mol) of styrene, 78.1 g (1 mol) of 2-mercaptoethanol, 4.1 g of azodiisobutyronitrile and 310 g of xylene is added. After the end of the addition, reaction continues for about 15 minutes; subsequently, 0.16 g of methylhydroquinone is added.

Excess monomer, xylene and residues of 2-mercaptoethanol are removed by distillation in vacuo and the colorless, viscous liquid which remains is finally diluted with xylene to a solids content of about 80%.

The molecular weight Mn determined from the hydroxyl number is 700 g/mol. The value for the molecular weight as determined by vapor pressure osmometry is 720 g/mol.

The solution of 700 g (about 1 mol) of the ω-hydroxy-functional polystyrene in 175 g of xylene and 35.0 g of potassium methylate (about 0.5 mol) are placed in a thoroughly dried stainless steel reactor which is additionally fitted with a stirrer. Azeotropic distillation is used to remove both traces of water and methanol together with xylene. Subsequently, a temperature of 80° C. is established and about 2000 g of ethylene oxide (about 45.5 mol) are added with stirring at a rate such that the internal reactor temperature does not exceed 85° C. and the pressure does not exceed 6 bar. After all of the ethylene oxide has been introduced, the temperature is held at 80° C. until a constant pressure indicates the end of the subsequent reaction. 100 g of water are added to the resulting product, which is then brought to a pH of from 6 to 7 with 30% phosphoric acid. The water is removed by azeotropic distillation in vacuo, and the salt which precipitates is removed by filtration.

The molecular weight determined from the hydroxyl number, at an assumed functionality of 1, is 2650; the gel permeation chromatogram shows only one maximum and gives a value of 3100 for Mn (calibration against PS); a value of 1.14 is obtained for the ratio Mw/Mn.

b) Preparation of the phosphoric ester 2650 g (corresponding to 1 OH equivalent) of the block copolymer are placed in the reactor, about 50 ml of toluene are added, and this initial charge is heated to 120° C. A vacuum is applied to remove all of the volatile fractions, especially water which may be present in the product, from the reaction chamber by distillation. After blanketing with nitrogen, the temperature of the contents is stabilized at 80° C. and 85 g of liquid polyphosphoric acid (0.25 mol $P_4O_{10}$; manufacturer: Merck; purity calculated as $P_4O10$: about 85%) are added.

After 2 hours the reaction is at an end. The acid number of the resulting material is 41 mg of KOH/g. An aliphatic hydroxyl group can no longer be detected in the $^1$H-NMR spectrum.

Table 1 shows examples of some phosphoric esters based on some polystyrene-b-polyalkylene oxide copolymers, as obtained by the above preparation process. The table indicates the molecular weights of the polystyrene segment and the chemical nature and molecular weight of the corresponding alkylene oxide.

TABLE 1

| Phosphoric ester | Mn (polystyrene segment)[1] | Mn (polyalkylene oxide segment)[1] | Alkylene oxide |
|---|---|---|---|
| 1A | 700 | 2000 | EO[2] |
| 2A | 700 | 1000 | EO |
| 3A | 1000 | 1000 | EO |
| 4A | 1000 | 1000 | EO/PO[3] (1:1)[4] |
| 5A | 1000 | 4000 | EO |
| 6A | 400 | 1000 | EO |
| 7A | 400 | 1800 | EO |

[1]The molecular weight is calculated from the determination of the hydroxyl number
[2]EO = ethylene oxide
[3]PO = propylene oxide
[4]Addition of a mixture of EO and PO; 1:1 denotes the molar ratio of EO to PO 2) Preparation of polystyrene oxide-b-polyalkylene oxide copolymers (not in accordance with the invention) as starting materials in the preparation of the corresponding phosphoric esters of the invention 128 g (1.72 mol) of butanol and 12.2 g (0.17 mol) of potassium methylate are placed in a reactor under a nitrogen atmosphere. After careful flushing with ultrapure nitrogen, this initial charge is heated to 110° C. and 854 g (7.1 mol) of styrene oxide are added over the course of one hour. After a further two hours the addition reaction of the styrene oxide is at an end, evident from a residual styrene oxide content of less than 0.1% (GC). Subsequently, 2847 g (64.6 mol) of ethylene oxide are metered into the reactor at a rate such that the internal temperature does not exceed 120° C. and the pressure does not exceed 6 bar. After all the ethylene oxide has been introduced, the temperature is held at 115° C. until a constant manometer pressure indicates the end of the subsequent reaction. Finally, the unreacted monomers are removed in vacuo at from 80 to 90° C.

The resulting product is neutralized using phosphoric acid and the water is removed by distillation, and the resultant potassium phosphate is removed by filtration together with a filtering aid. The molecular weight determined from the hydroxyl number (Mn/OH number), at an assumed functionality of 1, is 1950.

b) Preparation of the phosphoric ester

The preparation of the phosphoric ester takes place as described under 1b).

Table 2 shows examples of some phosphoric esters based on polystyrene oxide-b-polyalkylene oxide copolymers, as obtained by the above preparation process. The table indicates the molecular weights of the polystyrene segment and the chemical nature and molecular weight of the corresponding alkylene oxide.

TABLE 2

| Phosphoric ester | Mn (polystyrene oxide segment)[1] | Mn (polyalkylene oxide segment)[1] | Alkylene oxide |
|---|---|---|---|
| 1B | 450 | 1500 | EO[2] |
| 2B[3] | 450 | 1500 | EO |
| 3B | 630 | 1100 | EO/BO[4] (3:1)[5] |

[1]The molecular weight is calculated from the determination of the hydroxyl number
[2]EO = ethylene oxide
[3]Block structure by way of 1. ethylene oxide, 2. styrene oxide
[4]BO = butylene oxide
[5]Addition of a mixture of EO and BO; 3:1 denotes the molar ratio of EO to BO Performance Examples The effectiveness of the dispersants to be used in accordance with the invention is examined in accordance with various methods which describe typical applications in the plastics or coatings sector.

Method 1:

The fillers (or pigments) are treated with a solution of the test dispersant in toluene. The toluene is then distilled off and the surface-treated material is dried in vacuo. The solids coated in this way are ground in an ultracentrifugal mill (screen size 0.5 mm) in each case to the same agglomerate size. Subsequently, the ground solids are dispersed in liquid paraffin (30 cP) using a mizer disk first for 2 minutes at 2000 rpm and then 3 minutes at 4000 rpm. For the experiments in accordance with Method 1 calcium carbonate and aluminum hydroxide are coated, specifically calcium carbonate ($CaCO_3$) with 2% by weight of dispersant and aluminum hydroxide (ATH) with 1% by weight of dispersant.

The viscosities are measured with a Brookfield spindle viscometer (model LVT) at 23° C. and a rotary speed of 30 rpm with spindles of size No. 3 or No. 4. Table 3 indicates the viscosities of the liquid paraffin dispersions filled with the corresponding solids.

TABLE 3

| Phosphoric ester | Filler | Level of filling, % | Viscosity/mPas |
|---|---|---|---|
| — | ATH/$CaCO_3$ | 45 | n.d. |
| 1A | $CaCO_3$ | 55 | 720 |
| 3A | $CaCO_3$ | 55 | 410 |
| 3A | ATH | 65 | 660 |
| 6A | $CaCO_3$ | 55 | 520 |
| Stearic acid | $CaCO_3$ | 55 | 6900 |
| 1B | $CaCO_3$ | 55 | 560 |
| 3B | $CaCO_3$ | 55 | 820 |

n.d. = not determinable: dispersion highly viscous to solid

Method 2:

The fillers are added to a defined mixture which comprises not only the other formulating constituents but also the dispersant, using a stirring motor with a dispersing disk (ϕ50 mm) at a speed of rotation of about 1000 (rpm). For the performance experiments, mixtures are chosen comprising:

60 parts of unsaturated polyester resin (Palapreg P 17-02 or Palapreg P 14-01; manufacturer: BASF)

40 parts of thermoplastic component (Palapreg H 814-01: polystyrene, dissolved in styrene, or Palapreg H 850-01: polymethyl methacrylate, dissolved in styrene; manufacturer: BASF)

4.5 parts of zinc stearate 1.5 parts of t-butyl perbenzoate 180 parts of filler (calcium carbonate/Millicarb OG, manufacturer: Omya or aluminum hydroxide/Martinal ON 310; manufacturer: Martinswerke) and X parts of phosphoric esters of the invention.

In this case the viscosities are measured with a Brookfield spindle viscometer (model DV-I) at 23° C. and a rotary speed of 50 rpm with a spindle of type RVT-7. The viscosities are measured after a storage period of 10 minutes. Tables 4 to 7 show the viscosities of the various formulations, corresponding to the above formulation variants. In all cases the extent of reduction in viscosity obtainable with the dispersion of the invention is significant.

TABLE 4

(UP resin: Palapreg P 17-02/thermoplastic component: polystyrene/filler:calcium carbonate)

| Phosphoric ester | Amount/X parts | Viscosity (mPas) |
|---|---|---|
| — | — | 81000 |
| 2A | 1.8 | 29000 |
| 3A | 1.8 | 44500 |
| 5A | 1.8 | 51500 |
| 6A | 1.8 | 21000 |
| 7A | 0.9 | 28500 |
| 7A | 1.8 | 18000 |
| 7A | 2.7 | 16000 |
| 1B | 1.8 | 18500 |

TABLE 5

(UP resin: Palapreg P 14-01/thermoplastic component: polystyrene/filler:calcium carbonate)

| Phosphoric ester | Amount/X parts | Viscosity (mPas) |
|---|---|---|
| — | — | 120000 |
| 4A | 1.8 | 28500 |
| 7A | 1.8 | 21000 |
| 7A | 2.7 | 18000 |
| 1B | 1.8 | 19500 |
| 2B | 1.8 | 19000 |

TABLE 6

(UP resin: Palapreg P 17-02/thermoplastic component: polystyrene/filler:ATH

| Phosphoric ester | Amount/X parts | Viscosity (mPas/10 rpm) |
|---|---|---|
| — | — | 240000 |
| 4A | 1.8 | 50500 |
| 7A | 1.8 | 33000 |
| 7A[1] | 5.2 | 255000 |
| 1B | 2.7 | 19000 |
| 3B | 1.8 | 21000 |

[1]Formulation contains 350 parts of ATH/5.2 parts correspond in this way to 1.5% based on filler

TABLE 7

(UP resin: Palapreg P 17-02/thermoplastic component: polymethyl methacrylate/filler:ATH)

| Phosphoric ester | Amount/X parts | Viscosity (mPas) |
|---|---|---|
| — | — | 54000 |
| 1A | 1.8 | 30000 |
| 7A | 1.8 | 27000 |
| 2B | 1.8 | 19000 |

Method 3:

Preparation of pigment pastes

To prepare the pigment pastes, the dispersing additives are dissolved beforehand 40% strength in water, mixed with water and, if desired, with antifoams, and then the pigments are added. The dispersion takes place following the addition of grinding media (glass beads 2 to 3 mm, same volume as the pigment paste) for one (titanium dioxide) or two hours (other pigments) in a Skandex vibrator with air cooling.

Formulation of the white pastes

The white pastes are formulated as follows (amounts in % by wt.):

16.4 Water 12.3 Additive solution, 40% strength 1.0 Defoamer (e.g., Tego Foamex 810, Tego Chemie Service GmbH)

70.0 Titanium dioxide 2160 (Kronos)

0.3 Aerosil A 200 (fumed silica, Degussa)

Formulation of the black pastes

The black pastes are formulated as follows (amounts in % by wt.):

60.3 Water 22.3 (Dispersing) additive solution, 40% strength 1.0 Defoamer (e.g., Tego Foamex 810, Tego Chemie Service GmbH)

1.4 2-Amino-2-methylpropanol (Angus)

15.0 Pigmentary carbon black FW 200 (Dugussa)

Test coating materials

Transparent stoving enamel based on a modified alkyd resin (amounts in % by wt):

70.88 Alkyd resin Resydrol VWA 5477, 40% strength (Hoechst)

0.14 Defoamer (e.g. Byk 020, Byk-Chemie)

0.68 Thickener Bentone SD 1 (Rheox)

8.24 Melamine resin Maprenal MF 900 (Hoechst)

0.14 Triethanolamine 19.10 Water 0.68 Defoamer Additol XW 395 (Hoechst)

0.14 Leveling agent Additol XW 329 (Hoechst)

Introduce item 1 and add the other components with stirring.

Transparent emulsion varnish 97.0 Acrylate dispersion Neocryl XK 90 (Zeneca)

3.0 Texanol (ester alcohol, Eastman)

To prepare paints with gray pigmentation, 40.0 g of transparent enamel or varnish, respectively, 14.2 g of white paste and 2.65 g of black paste are added, and the mixture is homogenized at 1500 rpm for 5 minutes. The samples are knife-coated onto aluminum panels in a wet film thickness of 100 μm and are either stoved at 150° C. for 15 minutes following a flash-off time of 20 minutes (stoving enamel) or dried at room temperature (emulsion paint).

Test of paste stabilities

To determine the paste stabilities, the achievable initial viscosities and the viscosities after storage at 50° C. for four weeks are determined at two different shear rates (20 l/s and 1000 l/s).

| | White pastes | | | |
|---|---|---|---|---|
| Sample | Viscosity/ dPas immediate at 20 l/s | Viscosity/ dPas immediate at 1000 l/s | Viscosity/ dPas after 4 wk 50° C. at 20 l/s | Viscosity/ dPas after 4 wk 50° C. at 1000 l/s |
| 1A | 3.0 | 0.6 | 3.4 | 0.7 |
| 2A | 3.1 | 0.5 | 3.3 | 0.4 |
| 3A | 3.3 | 0.7 | 3.5 | 0.7 |
| 4A | 3.0 | 0.5 | 3.2 | 0.5 |
| 5A | 3.6 | 0.6 | 3.8 | 0.7 |
| 6A | 3.1 | 0.4 | 3.2 | 0.4 |
| 7A | 3.3 | 0.5 | 3.4 | 0.6 |
| 1B | 3.6 | 0.5 | 3.8 | 0.5 |
| 2B | 3.5 | 0.6 | 3.6 | 0.6 |
| 3B | 3.4 | 0.4 | 3.3 | 0.5 |
| Polystyrene-b-polyalkylene oxide copolymer precursor to 1A | 3.3 | 0.4 | 3.7 | 0.4 |
| Polystyrene-b-polyakylene oxide copolymer precursor to 3A | 3.5 | 0.6 | 3.8 | 0.7 |
| Fatty acid alkoxylate | 2.8 | 0.5 | 5.5 | 1.0 |
| Modified acrylate polymer | 4.2 | 1.3 | 6.8 | 1.5 |

-continued

| | Black pastes | | | |
|---|---|---|---|---|
| Sample | Viscosity/ dPas immediate at 20 l/s | Viscosity/ dPas immediate at 1000 l/s | Viscosity/ dPas after 4 wk 50° C. at 20 l/s | Viscosity/ dPas after 4 wk 50° C. at 1000 l/s |
| 1A | 2.2 | 0.6 | 2.3 | 0.6 |
| 2A | 2.3 | 0.6 | 2.5 | 0.7 |
| 3A | 2.0 | 0.5 | 2.1 | 0.6 |
| 4A | 2.4 | 0.7 | 2.4 | 0.7 |
| 5A | 2.3 | 0.5 | 2.5 | 0.6 |
| 6A | 1.9 | 0.5 | 2.0 | 0.6 |
| 7A | 2.0 | 0.6 | 2.1 | 0.6 |
| 1B | 2.3 | 0.7 | 2.4 | 0.7 |
| 2B | 2.2 | 0.6 | 2.3 | 0.7 |
| 3B | 2.0 | 0.6 | 2.2 | 0.7 |
| Polystyrene-b-polyalkylene oxide copolymer precursor to 1A | 2.0 | 0.6 | 2.2 | 0.7 |
| Polystyrene-b-polyaklyene oxide copolymer precursor to 3A | 2.1 | 0.5 | 2.3 | 0.6 |
| Fatty acid alkoxylate | 1.8 | 0.4 | 2.5 | 0.6 |
| Modified acrylate polymer | 3.7 | 0.8 | 4.4 | 1.0 |

The good stability of the pigment pastes of the invention is readily evident from the rise in viscosity, which is small in each case.

Test of dispersing properties

Application of the test formulations in a wet film thickness of 100 μm; drying for 6 minutes, then rubout test over ⅓ of the surface; after stoving or overnight drying, calorimetric determination of the films by means of a XP 68 spectrophotometer from X-Rite; determination of the degree of gloss and the haze by means of Haze-Gloss from Byk-Gardner.

| Stoving enamel based on Resydrol VWA 5477 | | | |
|---|---|---|---|
| Sample | Lightness L | Delta E after rubout | Degree of gloss (60° angle) |
| 1A | 41.5 | 0.4 | 53 |
| 2A | 42.3 | 0.3 | 51 |
| 3A | 41.8 | 0.4 | 55 |
| 4A | 43.2 | 0.4 | 53 |
| 5A | 41.7 | 0.3 | 55 |
| 6A | 40.9 | 0.5 | 54 |
| 7A | 41.2 | 0.3 | 56 |
| 1B | 42.2 | 0.3 | 54 |
| 2B | 43.0 | 0.4 | 53 |
| 3B | 42.8 | 0.3 | 53 |
| Polystyrene-b-polyalkylene oxide copolymer precursor to 1A | 44.0 | 0.6 | 51 |
| Polystyrene-b-polyalkylene oxide copolymer precursor to 3A | 44.2 | 0.5 | 52 |

-continued

| | | | |
|---|---|---|---|
| Fatty acid alkoxylate | 44.6 | 0.7 | 49 |
| Modified acrylate polymer | 44.9 | 0.4 | 55 |

Emulsion paint based on Neocryl XK 90

| Sample | Lightness L | Delta E after rubout | Degree of gloss (60° angle) | Haze |
|---|---|---|---|---|
| 1A | 47.5 | 0.3 | 40.5 | 110 |
| 2A | 47.6 | 0.4 | 42.0 | 115 |
| 3A | 47.3 | 0.5 | 41.0 | 110 |
| 4A | 47.9 | 0.3 | 39.0 | 120 |
| 5A | 47.6 | 0.4 | 42.0 | 125 |
| 6A | 47.7 | 0.5 | 41.5 | 115 |
| 7A | 47.5 | 0.4 | 42.0 | 110 |
| 1B | 48.0 | 0.4 | 40.5 | 120 |
| 2B | 48.2 | 0.5 | 39.0 | 110 |
| 3B | 48.1 | 0.4 | 42.5 | 125 |
| Polystyrene-b-polyalkylene oxide copolymer precursor to 1A | 48.3 | 0.7 | 39.0 | 120 |
| Polystyrene-b-polyalkylene oxide copolymer precursor to 3A | 48.4 | 0.8 | 39.5 | 125 |
| Fatty acid alkoxylate | 48.3 | 0.9 | 40.0 | 120 |
| Modified acrylate polymer | 49.0 | 0.4 | 40.5 | 130 |

The favorable development of color strength achievable through the use of the dispersing additives of the invention, and the rubout test, which is favorable in all cases, are evident.

This also becomes particularly marked in comparison with the commercial examples not in accordance with the invention: a fatty acid alkoxylate (Tego dispers 740W, Tego Chemie Service) and a modified acrylate (Tego Dispers 745W).

What is claimed is:

[1. A phosphoric ester having the formula:

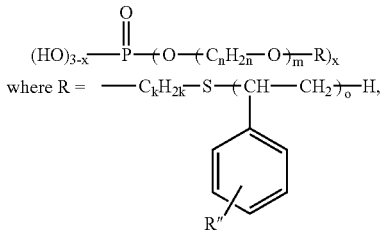

x is 1 or 2, n is a number from 2 to 18, m and o are each a number from 1 to 100, k is a number from 2 to 4, and R" is H or a linear or branched alkyl radical.

R' is an alkyl, alkaryl, alkenyl or sulfopropyl radical.]

2. The [phosphoric ester] *pigment preparation* of claim [1] *18* wherein the ratio of m/o is from 1:10 to 10:1.

3. The [phosphoric ester] *pigment preparation* of claim [1] *18* wherein the ratio of m/o is from 1:2 to 10:1.

[4. The phosphoric ester of claim 1 wherein the average molecular weight is from 300 to 15,000 g/mol.]

[5. The phosphoric ester of claim 1 wherein the average molecular weight is from 500 to 5000 g/mol.]

6. The phosphoric ester of claim [1] *17* wherein R"=H.

7. A method of forming a dispersion comprising dispersing a phosphoric ester of claim [1] *17* with one or more pigments or fillers in an aqueous or organic medium.

8. The method of claim 7 wherein R"=H.

9. A method of forming a highly filled sheet molding compound or bulk molding compound, comprising dispersing components of a molding compound and a phosphoric ester as of claim [1] *17*.

10. The method of claim 9 wherein R"=H.

[11. A pigment preparation comprising one or more organic or inorganic pigments and from 1 to 100% by weight, based on the pigments, of a dispersing additive having the formula:

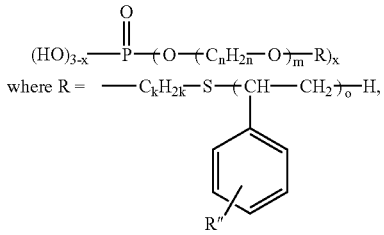

x is 1 to 2, n is a number from 2 to 18, m and o are each a number from 2 to 100, k is a number from 2 to 4, and R" is H or a linear or branched alkyl radical.]

12. The pigment preparation of claim [11] *18* wherein R"=H.

[13. An aqueous paste comprising one or more organic or inorganic colorants and from 1 to 100% by weight, based on the colorants, of a dispersing additive having the formula:

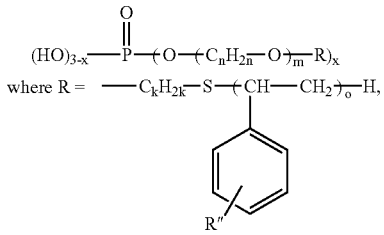

x is 1 to 2, n is a number from 2 to 18, m and o are each a number from 2 to 100, k is a number from 2 to 4, and R" is H or a linear or branched alkyl radical.]

14. An aqueous paste of claim [13] *19* wherein R"=H.

[15. A carbon black paste comprising from 10 to 100% by weight, based on the weight of carbon black, of a dispersing additive having the formula:

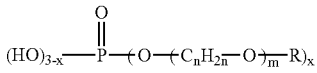

-continued where R = $-C_kH_{2k}-S-(CH-CH_2)_o-H$,

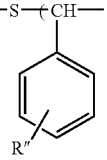

x is 1 or 2, n is a number from 2 to 18, m and o are each a number from 2 to 100, k is a number from 2 to 4, and R" is H or a linear or branched alkyl radical.]

16. A carbon black paste of claim [15] *20* wherein R"=H.

*17. A phosphoric ester having the formula:*

*(I)*

$(HO)_{3-x}-P(=O)-(O-(C_nH_{2n}-O)_m-R]_x$

*wherein R =* $-C_kH_{2k}-S-(CH-CH_2)_o-H$ *or,*

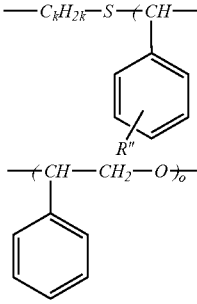

*x is 1 or 2,*

*n is a number from 2 to 18,*

*m and o are each a number from 2 to 100,*

*k is a number from 2 to 4,*

*R" is H or a linear or branched alkyl radical,*

*R' is an alkyl, alkaryl, alkenyl or sulfopropyl radical, and with the proviso that when R=*

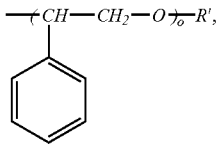

*the average molecular weight of said phosphoric ester is not more than about 2184 g/mol.*

*18. A pigment preparation comprising one or more organic or inorganic pigments and from 1 to 100% by weight, based on the pigments, of a dispersing additive having the formula:*

$(HO)_{3-x}-P(=O)-(O-(C_nH_{2n}-O)_m-R)_x$

-continued

*where R =* $-C_kH_{2k}-S-(CH-CH_2)_o-H$, *or,*

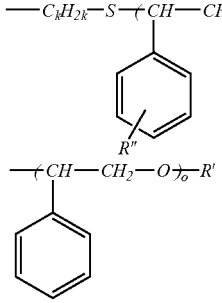

*x is 1 to 2,*

*n is a number from 2 to 18,*

*m and o are each a number from 2 to 100,*

*k is a number from 2 to 4,*

*R" is H or a linear or branched alkyl radical,*

*R' is an alkyl, alkaryl, alkenyl or sulfopropyl radical, and with the proviso that when R=*

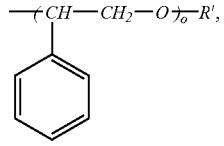

*the average molecular weight of said phosphoric ester is from 500 to 5000 g/mol.*

*19. An aqueous paste comprising one or more organic or inorganic colorants and from 1 to 100% by weight, based on the colorants, of a dispersing additive having the formula:*

$(HO)_{3-x}-P(=O)-(O-(C_nH_{2n}-O)_m-R)_x$

*where R =* $-C_kH_{2k}-S-(CH-CH_2)_o-H$, *or,*

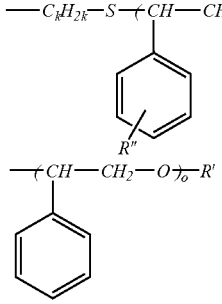

*x is 1 to 2,*

*n is a number from 2 to 18,*

*m and o are each a number from 2 to 100,*

*k is a number from 2 to 4,*

*R" is H or a linear or branched alkyl radical, and*

*R' is an alkyl, alkaryl, alkenyl or sulfopropyl radical.*

*20. A carbon black paste comprising from 10 to 100% by weight, based on the weight of carbon black, of a dispersing additive having the formula:*

$(HO)_{3-x}-P(=O)-(O-(C_nH_{2n}-O)_m-R)_x$

-continued where R = 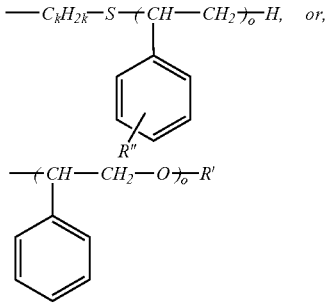

*x is 1 to 2,*

*n is a number from 2 to 18,*

*m and o are each a number from 2 to 100,*

*k is a number from 2 to 4,*

*R″ is H or a linear or branched alkyl radical, and*

*R′ is an alkyl, alkaryl, alkenyl or sulfopropyl radical.*

*21. The phosphoric ester of claim 17, wherein o is not less than 4.*

*22. The aqueous paste of claim 19 wherein the ratio of m/o is from 1:10 to 10:1.*

*23. The aqueous paste of claim 19 wherein the ratio of m/o is from 1:2 to 10:1.*

*24. The carbon black paste of claim 20 wherein the ratio of m/o is from 1:10 to 10:1.*

*25. The carbon black paste of claim 20 wherein the ratio of m/o is from 1:2 to 10:1.*

* * * * *